United States Patent [19]

Greenwald

[11] 4,032,437
[45] * June 28, 1977

[54] FECAL EXAMINATION DEVICE

[76] Inventor: Robert J. Greenwald, 4771 N. Federal Highway, Pompano Beach, Fla. 33064

[ * ] Notice: The portion of the term of this patent subsequent to June 25, 1991, has been disclaimed.

[22] Filed: Mar. 26, 1974

[21] Appl. No.: 455,016

Related U.S. Application Data

[63] Continuation-in-part of Ser. No. 150,357, June 7, 1977, abandoned, which is a continuation-in-part of Ser. No. 255,857, May 22, 1972, Pat. No. 3,819,045.

[52] U.S. Cl. .................................. 209/17; 209/173
[51] Int. Cl.² ............................................ B03B 7/00
[58] Field of Search ............... 209/2, 3, 5, 17, 173, 209/273, 268, 250, 237, 315, 162, 163, 172, 269; 23/230 B, 292; 220/4 R, 4 A, 5 R, 8, 42 A, 42 B, 42 C, 69; 229/1.5 C; 73/425, 425.2, 425.4 R; 210/359, DIG. 24, 515-518, 83

[56] References Cited

UNITED STATES PATENTS

| | | | |
|---|---|---|---|
| 539,779 | 5/1895 | Shugerman | 210/515 |
| 879,753 | 2/1908 | Eckert | 220/8 |
| 2,196,451 | 4/1940 | Holzer | 209/17 |
| 2,438,434 | 3/1948 | Friedman | 220/8 |
| 3,285,459 | 11/1966 | Gahm | 220/8 |
| 3,380,592 | 4/1968 | Arnold | 210/359 X |
| 3,819,045 | 6/1974 | Greenwald | 209/17 |

FOREIGN PATENTS OR APPLICATIONS

| 62,995 | 7/1892 | Germany | 210/359 |
|---|---|---|---|

OTHER PUBLICATIONS

American Public Health Ass'n, Diagnostic Procedures and Reagents, 3rd ed. N.Y. 1950, p. 421.
Bray's Clinical Laboratory Methods, 6th ed. Cu Mosby Co., 1962, pp. 336–337.

Primary Examiner—Frank W. Lutter
Assistant Examiner—Ralph J. Hill
Attorney, Agent, or Firm—Abner Sheffer

[57] ABSTRACT

A fecal examining device comprising a closure member in the form of a tray adapted to be fitted upon the open lower end of a solution-receiving receptacle or cylinder, said closure member or tray including a central, open-top cup that extends into the cylinder for a short, predetermined distance. A cap is provided for closing the open top of the cup or well when the tray is not attached to the cylinder. A perforated piston is provided for manual movement within the cylinder to thereby separate ova from the fecal material in solution.

2 Claims, 6 Drawing Figures

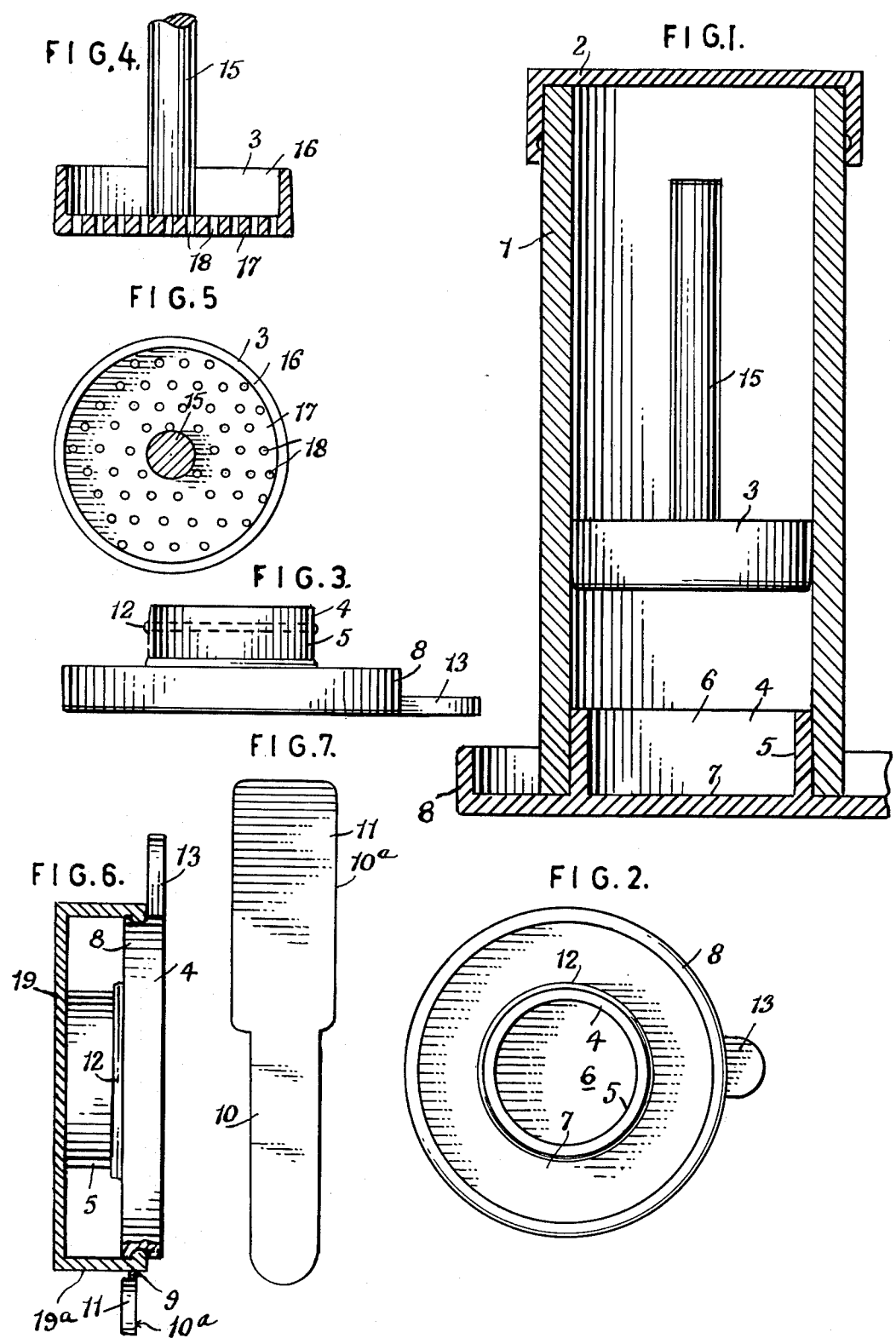

FECAL EXAMINATION DEVICE

This application is a continuation-in-part of my copending applications Ser. No. 150,357 filed June 7, 1971, now abandoned, which is a continuation-in-part of Ser. No. 255,857 filed May 22, 1972, now U.S. Pat. No. 3,819,045 of June 25, 1974 whose entire disclosures are incorporated herein by reference.

BACKGROUND OF THE INVENTION

The present invention relates to means for examining and analyzing fecal matter and has for its object to provide a device which will simplify and render effective the securement of, separation of, the feces from the ova or eggs of parasites such as might be contained within the fecal matter.

At the present time, the examination of fecal matter is had by a patient being given a disposable container which he returns containing a specimen, to a physician or laboratory. A measured amount of the fecal matter is then placed in another container and is thoroughly mixed into a solution with a specific gravity greater than water to thereby float the ova from the broken up specimen.

The strained solution is then filtered through a strainer into another container. The strained solution is then poured into still another container to the point of overfilling; namely, a convex meniscus. A slide is then placed on the meniscus and is allowed to stand for at least ten minutes and it is then removed with some of the solution adhering to it. A cover slip is then placed on the slide and it is examined under a microscope.

With the device of the present invention, a number of the steps customarily pursued, are eliminated and the procedure involved is simplified. The patient is given a disposable fecal unit which will hold only the desired amount of the fecal matter. The bottom of the unit which constitutes a tray or holder for the fecal matter is placed on the lower end of a cylinder and solution is poured into the cylinder. The cylinder can be, if and when necessary, provided with a removable closure cap at the top.

The cylinder is half filled with flotation solution and mixed thoroughly with the feces. The foraminous-bottom piston or strainer is placed within the cylinder and is pushed downwardly to a variable point below the fluid level. The cylinder is then filled to a point of meniscus, and a slide is placed on the meniscus to be later removed with solution adhering to it. A coverslip is placed on the slide and the slide examined under the microscope.

Reference is to be had to the accompanying drawing in which an illustrative embodiment of the invention is shown and in which:

FIG. 1 is a longitudinal sectional view through a fecal examining device constructed in accordance with the invention.

FIG. 2 is a top plan view of the combined fecal holder or tray that forms the bottom closure for the cylinder;

FIG. 3 is an elevational view of the tray or holder of FIG. 2;

FIG. 4 is a sectional view through the strainer piston;

FIG. 5 is a top plan view of the strainer piston, with the stem or rod thereon being shown in section;

FIG. 6 is a side view of the tray or holder showing a closure cap fitted over the normally open top of the cup on the tray; and, FIG. 7 is a face view of the detached paddle or scoop.

The device as shown, consists of four main elements; namely, a mixing chamber or container in the form of a cylinder or tube 1; a bottom closure member or tray 4 constituting a carrier for the fecal matter; a piston-like strainer 3, and a closure cap 19 for the top of the tray 4.

The body of the device, consisting of the cylinder 1, may be made of any suitable material and is preferably of a transparent nature to permit the mixing operation to be observed. The cylinder 1 is open at its opposite ends and if and when desired the upper end can be closed by means of a conventional snap-on type of closure cap 2.

The lower end of the cylinder 1 is adapted to be closed during the use of the device by means of a tray-like closure member or fecal holder 4 shown in detail in FIGS. 2 and 3. Said tray or holder includes an outer peripheral wall or flange 8 and disposed within, and located concentrically of the wall or flange 8, is an inner and higher annular wall 5 that cooperates with a bottom wall or floor 7 in forming an open-top well 6.

Extending laterally from the side wall 19a of a closure cap 19 for the tray or holder 4 is a frangible neck 9 (FIG. 6), which connects to a removable paddle or scoop 10a provided with a handle portion 10 and head 11. The paddle or scoop 10a can be separated when needed from the cover or closure cap 19 by fracture of the neck 9.

The tray or holder 4 can be applied to the end of the cylinder 1 with a tight or force fit provided with any type detent means if necessary to engage with the inner wall surface of the cylinder 1 near the lower end thereof. After the tray 4 containing the fecal matter is fitted in place on the end of the cylinder, the wall 5 will very closely fit within the cylinder and will extend upwardly therein for a short distance and it will frictionally engage against the inner surface of the cylinder wall so that a positive prevention of leakeage will be effected. The finger piece 13 is for the removal of the bottom tray from closure 19.

The piston-like strainer generally indicated at 3, has a cup-shaped body provided with a circumferential wall 16 and a perforated or foraminous bottom wall 17 having thus a plurality of holes 18. Located centrally of the body of the strainer is a vertical or upstanding stem or rod 15 by means of which the strainer can be manipulated.

The tray or holder 4 of the device may be made of disposable material and when filled and capped by the closure cap 19 and returned by the patient, it is placed on the bottom of the cylinder 1 as shown in FIG. 1, with the open top of the wall 6 facing upwardly within the cylinder.

The closure cap 19 has its circumferential wall 19a arranged to fit over the wall 8 so that when the closure cap is in place it fits over the entire top of the tray 4, thus closing the well 6, as well as the space between the walls 5 and 8.

The tray or holder 4 which then constitutes the closure member for the lower end of the cylinder during the separation of the feces is thus the carrier for the fecal matter. When the well 6 is filled with the fecal matter by the patient, the top of the well is covered or closed by the closure cap 19. The closure cap 19 can be a snap-on type.

The tray or holder 4 has an area which extends laterally beyond the cylinder when fitted thereon and the tray is thus made of a sufficient diameter to enable it to act as a supporting base for the cylinder, preventing it from tipping over. It also serves to collect any of the solution that might drip off when the slide is placed in position. The paddle or scoop 11, being connected to closure cap 19 by a frangible neck 9, can be torn off and be used to transfer feces to the container.

The strainer 3 acts as a piston and snugly but slidably fits within the cylinder and can be pushed down into the cylinder to the required extent and below the level of the fecal matter mixture by means of the attached rod 15. The eggs in such mixture have a specific gravity less than that of the solution and thus will continually strain upwardly toward the slide. The number and size of the holes 18 can be varied, the purpose of the strainer 3 being to keep fecal material from floating upwardly with the eggs.

When the solution is placed in the cylinder the feces is broken up and the strainer is placed in the solution. Solution is added until it forms a meniscus at the point of overfilling. A slide is then placed on the cylinder in contact with the solution and after ten minutes the slide will be ready to read.

It is to be noted that the cylinder 1 need not be separated from the tray during the testing procedure, but is easily removable for cleaning if not composed of readily disposable material.

Floatation or levitation of parasite ova or eggs can be accomplished by various substances. Solutions of sodium nitrate or sucrose, or magnesium sulfate, or zinc sulfate, or sodium chloride can be used. Each of these has its own merits and what might be used is a matter of personal preference. The main purpose of the solute is to raise the specific gravity to, say, approximately 1.18, so that the ova will float to the top.

The structure of the present invention is such that the parts thereof may be made readily disposable and there is a minimal handling of obnoxious material. Continuous straining or filtration during the floatation period occurs as ova seek to reach the surface by passing through the strainer. The tray 4, fitted on the end of the cylinder adds stability to the device and is arranged to catch any overflow of the fecal matter. The closure cap 19 for the tray can receive the name of the patient to thus identify the specimen. These and other advantages will be apparent to those skilled in this art.

The device is particularly suitable for use in veterinary work as in analyzing the feces of dogs or cats for the presence of ova, larvae, and parasites, such as the cysts of certain protozoans. It is also suitable for use in analyzing human feces.

In a preferred form, the device is made entirely of plastic material. For instance the tray 4 and closure cap 19 may be of a tough high polymer, e.g. a thermoplastic polymer such as polyethylene, and may be produced by injection molding. Either the tray 4 or the closure cap 19 may carry thereon indicia giving directions for the use of the device to the dog owner. Thus, in one preferred form printed directions, as follows, are molded into the outwardly facing surface of cap 19: "Directions Place B.M. in Small Center Receptacle"; also molded into the same surface of cap 19 is the word "Name" next to which there is an unmarked area preferably having a relatively rough or microscopically pitted surface adapted to receive and hold ink, so that the name of the dog and/or owner can be written thereon, using a marking pen, before the assemblage of tray 4 and closure cap 19 is sent to the laboratory for analysis. The other surfaces of the tray and cap preferably have the usual relatively smooth finish imparted by contact with the polished metal mold during the molding operation.

In a preferred form of the device the tube or cylinder 1 is also of a tough high polymer, e.g. a thermoplastic polymer such as stereoregular polypropylene. While the latter material is often somewhat cloudy in appearance it is transparent enough for the analyst to see through it to observe the liquid level. The tight press fit between the tube 1 and the outer face of the annular wall 5 is facilitated by the fact that these elements are made of materials which differ in rigidity or hardness so that one element (e.g. the softer polyethylene) yields to conform to the other; to this end the internal diameter of the bottom of the tube is made slightly less than the external diameter of the wall 5, the dimensions being such that the force fit can be effected by hand pressure.

The whole device is so constructed and of such size that the various parts may be easily manipulated by hand and may be produced at low cost; thus, they are economical to use despite the fact that they are thrown away after a single use.

The well 6 preferably has an interior volume in the range of about one half to 5 cc, more preferably about 2 cc. Its internal diameter is preferably about 0.5 to 5 cm, more preferably about 1 to 2 cm (e.g. 1.5 cm). The ratio of the interior volume of the cylinder 1 to the interior volume of the well 6 is preferably at least about 2:1, more preferably above 3:1, e.g. above 5:1 or 7:1 such as about 10:1. These ratios are such as to provide for adequate fluidity of the mixture of feces and diluent. Thus when the cylinder is partially filled (e.g. half filled) with diluent after being fitted to the well and the feces are then stirred and broken up in the diluent (as by means of a suitable thin rod) the mixture of feces and diluent will be neither too thick nor too thin for analysis according to the invention. The high ratios obviously permit greater dilution of the feces which is desirable in that the specific gravity of the diluent is not affected as much by the varying water contents of the individual feces samples and floatation of ova is thereby improved. For practical purposes higher ratios above about 10:1 or 20:1 do not provide sufficient additional benefit and may make the device unnecessarily bulky; thus it is preferred that the ratio be well below about 100:1.

The head portion 11 of paddle 10a is of a size adapted to carry the amount of feces which can fit into the well 6. Its width is a substantial fraction (e.g. more than one-fifth) of the diameter of the well 6, but is preferably not greater than the diameter of the well 6 so that it will pick up a mass of fecal material narrow enough to be transferred into the well without smearing the outer walls of the well. It is flat and serves as a spatula, thus permitting the user to employ it to pat down the fecal mass flat into the well and avoid having a projecting mound of feces extending above the top of the well.

The strainer 3 is preferably likewise made of plastic material like that of the other parts, e.g. tough but flexible polyethylene. Its circumferential wall, or skirt, 17 functions to stabilize the strainer in its downward passage and reduce tilting thereof thus reducing any tendency for fecal material to become wedged between the outer wall of the strainer and the inner wall of the tube. It is also within the broader scope of the invention for the skirt to have a thin outwardly extending integral circumferential fin to aid in sweeping downward any such fecal material that may be situated along the inner wall of the tube; also the strainer may comprise a pair of parallel horizontal apertured strainer plates mounted, say about 1 to 2 cm apart on a central vertical manipulating rod, both such plates conforming to the size and shape of the inner wall of the tube and both preferably being integrally molded with the rod, without any skirt.

The holes 18 preferably have diameters well above 0.5 mm and well below 1.5 mm. Particularly suitable are holes having diameters of about 1 mm. By experimentation I have found that holes of such size are large enough not to be clogged by fecal debris, such as the mucous and slime that are present in some dog feces, and at the same time are not large enough to permit the passage, by floatation through the holes, of such an amount of fecal matter as to significantly interfere with the microscopic examination. Preferably the holes are closely spaced and substantially the entire face of the bottom wall is perforated, as is indicated in FIG. 5 of the drawing.

The rod portion 15 of strainer 3 is preferably appreciably shorter than the height of the cylinder. Thus, when the strainer is placed in the cylinder it can be pushed down to force the suspended fecal matter toward the bottom of the cylinder (allowing parasite eggs, in the diluent, to pass through the holes in the strainer) until the top of the rod portion 15 is below the top of the cylinder. In this position the top of the rod portion will not interfere with the meniscus or with the slide which is placed on top of the cylinder. The top of the cylinder like its bottom, is preferably at a right angle to the axis of the cylinder (as shown in the drawing) so that the slide placed thereon will be substantially level. It will be understood that the diameter of the top of the cylinder may be made larger than that of the bottom. Thus it is advantageous to make the cylinder very slightly larger at the top, e.g. for ease of molding.

As mentioned previously the tray or holder 4 is of such outer dimensions as to form a stable supporting base for the cylinder, even when a microscope slide is placed on top of the latter. In one typical embodiment this base is about 4 cm across while the cylinder is about 5 (e.g. 5.5) cm high and about 2 to 3 cm in external diameter.

Methods for fecal analysis without the use of a filtering element are known in the art, e.g. the "Willis technique". While less desirable, it is within the broader scope of the invention to employ the device and process of the invention without a filter. The microscope slide (which may be the cover glass portion thereof) becomes rather dirty of course but the ova can be detected thereon if numerous enough. When no filter is employed the other steps of the new process are otherwise substantially the same as described herein; the use of the novel combination of feces collection cup and attachable tube will still make things much easier and neater for both the sample collector and the analyst.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

I claim:

1. A fecal examining process for detecting the presence of parasite material in feces, comprising providing cup means for receiving and transporting a sample of feces to be examined, providing a tube, open at both its ends, constructed and arranged to be tightly fitted to said cup means so that when so fitted the cup means closes one end of said tube and serves as a base for said tube whereby liquid diluent can then be poured into the other end of the tube to mix with the feces and be retained in the tube by the presence of said cup means, placing a sample of the feces to be examined in said cup means, then fitting said tube to said cup means, pouring liquid diluent into said tube to mix with the feces sample in said cup means, and permitting parasite material to float upward in said tube, through liquid diluent of higher density than said parasite material, to a collecting surface.

2. A fecal examining device comprising cup means for receiving and transporting a sample of feces to be examined, and a tube, open at both its ends, constructed and arranged to be fitted to said cup means after said sample is placed in, and transported in, said cup means with said cup means tightly closing one end of said tube and serving as a base for said tube whereby liquid diluent can then be poured into the other end of the tube to mix with the feces and be retained in the tube by the presence of said cup means, said tube having strainer means therein to retain fecal material below while permitting diluent liquid and ova present in the feces to pass through said strainer means.

* * * * *